United States Patent [19]
Conder et al.

[11] Patent Number: 5,643,940
[45] Date of Patent: Jul. 1, 1997

[54] DIOXAPYRROLOMYCIN AS AN ANTIPARASITIC AGENT AND COMPOSITIONS USEFUL THEREFOR

[75] Inventors: George Anthony Conder, Richland; Ming-Shang Thomas Kuo, Portage; Vincent P. Marshall, Kalamazoo; Raymond John Zielinski, Portage, all of Mich.

[73] Assignee: The Upjohn Company, Kalamazoo, Mich.

[21] Appl. No.: 432,374

[22] Filed: May 1, 1995

Related U.S. Application Data

[63] Continuation of Ser. No. 189,694, Feb. 1, 1994, abandoned, which is a continuation-in-part of Ser. No. 739,765, filed as PCT/US92/06290, Aug. 3, 1992, abandoned.

[51] Int. Cl.$^6$ ............................................. A61K 31/40
[52] U.S. Cl. ............................................. 514/422
[58] Field of Search ............................................. 514/422

[56] References Cited

U.S. PATENT DOCUMENTS 4,495,358   1/1985   Koyama et al. ............................ 548/550

FOREIGN PATENT DOCUMENTS 0 080 051   10/1982   European Pat. Off. .
2 111 985    7/1983   United Kingdom .

OTHER PUBLICATIONS

The Journal of Antibiotics, vol. XXXIV No. 10, "New Chlorinated Nitro–Pyrrole Antibiotics, Pyrrolomycin A and B (SF–2080 A and B)", N. Ezaki, et al., pp. 1363–1365, (1981).

The Journal of Antibiotics, vol. XXXIV No. 10, "Structure of Pyrrolomycin B, A Chlorinated Nitro–Pyrrole Antibiotic", M. Kaneda, et al., pp. 1366–1368, (1981).

The Journal of Antibiotics, vol. XXXIV No. 12, "Structure and Synthesis of Pyrrolomycin A. A Chlorinated Nitro–pyrrole Antibiotic", M. Koyama, et al., pp. 1569–1576, (1981).

The Journal of Antibiotics, vol. XXXVII No. 10, "Enhancement of Mouse Immune System by Pyrrolomycin B", M. Ishizuka, et al., pp. 1253–1256, (1984).

The Journal of Antibiotics, vol. XL No. 2, "LL–F42248α, A Novel Chlorinated Pyrrole Antibiotic", GT Carter, et al., pp. 233–236, (1987).

The Journal of Antibiotics, vol. XL No. 6, "Isolation and Characterization of a New Antibiotic, Dioxapyrrolomycin, Related to Pyrrolomycins", Hikaru Nakamura, et al., pp. 899–903, (1987).

ACS Meeting Abstracts 97, 98, 99 Spring 1991, Addar et al. J. Chem. Soc. Chem. Commun., "Direct Biochemical Nitration in the Biosynthesis of Dioxapyrrolomycin. A Unique Mechanism for the Introduction of Nitro Groups in Microbial Products", GT Carter, et al., pp. 1271–1273, (1989).

K. Masuda, et al., "Pyrrolomycin Group Antibiotics Inhibit Substance P–Induced Release of Myeloperoxidase From Human Polymorphonuclear Leukocytes", The Journal of Antibiotics, vol. 44, No. 5, pp. 533–540 (1991).

K. G. Simpkin et al., "The Use of Caenorhabditis Elegans for Anthelmintic Screening", Journal of Chemical Technology and Biotechnology, vol. 31, pp. 66–69 (1981).

K. Yano et al., "Pyrroxamycin, a New Antibiotic Taxonomy, Fermentation, Isolation, Structure Determination and Biological Properties", vol. KL, No. 7, pp. 961–969 (1987).

S. Rengaraju et al., "A New Antibiotic Al–R 2081 Related to Pyrrolomycin B", Meiji Seika Kenkyu Nenpo, India, vol. 24, pp. 48–51, (1985).

V.P. Marshall et al., "Current Fermentation Technology for the Production of Antibiotics from Actinomycetes: The Example of Paulomycin", Developments in Industrial Microbiology (Journal of Industrial Microbiology Suppl. No. 2), vol. 28, pp. 105–114 (1987).

*Primary Examiner*—Allen J. Robinson
*Attorney, Agent, or Firm*—James D. Darnley, Jr.; Martha A. Gammill

[57] ABSTRACT

This invention concerns a method for killing internal parasites, especially nematodes, trematodes and cestodes affecting warm blooded animals such as sheep, cattle, swine, goats, dogs, cats, horses and humans as well as poultry by administering an effective amount of dioxapyrrolomycin of the formula I. Anthelmintic compositions of dioxapyrrolomycin and an improvement in the process of preparation of dioxapyrrolomycin are also provided.

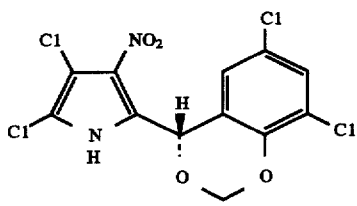

3 Claims, No Drawings

DIOXAPYRROLOMYCIN AS AN ANTIPARASITIC AGENT AND COMPOSITIONS USEFUL THEREFOR

CROSS REFERENCE TO RELATED APPLICATIONS

This application is a continuation of U.S. Ser. No. 08/189,694, filed Feb. 1, 1994, which is a continuation of International Application No. PCT/US92/06290, filed Aug. 3, 1992, which is a continuation-in-part of U.S. Ser. No. 07/739,765, filed Aug. 1, 1991, abandoned.

SUMMARY OF THE INVENTION

This invention pertains to a new method for killing and controlling worms (Helminths) and new compositions for killing and controlling worms in animals. The invention is more particularly directed to a new method for killing and controlling parasitic worms in animals with dioxapyrrolomycin and to new anthelmintic compositions comprising the same.

Dioxapyrrolomycin has the general structural formula I.

BACKGROUND OF THE INVENTION

The diseases or groups of diseases described generally as helminthiasis are due to infection of the animal parasitic worms known as helminths. Helminthiasis and helminthosis are prevalent and may lead to serious economic and/or health problems in sheep, swine, cattle, goats, dogs, cats, horses, poultry and man. Among the helminths, the groups of worms known as nematodes, trematodes and cestodes cause widespread and often-times serious infections in various species of animals including man. The most common genera of nematodes, trematodes and cestodes infecting the animals referred to above are Dictyocaulus, Haemonchus, Trichostrongylus, Ostertagia, Nematodirus, Cooperia, Bunostomum, Oesophagostomum, Chabertia, Strongyloides, Trichuris, Fasciola, Dicrocoelium, Enterobius, Ascaris, Toxascaris, Toxocara, Ascaridia, Capillaria, Heterakis, Ancylostoma, Uncinaria, Onchocerca, Taenia, Moniezia, Dipylidium, Metastrongylus, Hyostrongylus, and Strongylus. Some of these genera attack primarily the intestinal tract, while others inhabit the stomach, lungs, liver and subcutaneous tissues. The parasitic infections causing helminthiasis and helminthosis lead to anemia, malnutrition, weakness, weight loss, unthriftiness, severe damage to the gastrointestinal tract wall and, if left to run their course, may result in death of the infected animals.

The anthelmintic activity of dioxapyrrolomycin has not been previously reported.

INFORMATION DISCLOSURE

Pyrrolomycins, including dioxapyrrolomycin, pyrrolomycin C, and pyrrolomycin D, are known metabolites of Streptomyces sp.

The discover of dioxapyrrolomycin was reported originally by Lederle Lab, G. T. Carter, et al., J. Antibio. 40:233 (1987), under the name LL-F42248 alpha without any chemical name. Shortly after, the name of dioxapyrrolomycin was used in a report by the Institute of Microbial Chemistry, H. Nakamara, et al. J. Antibio. 40:899 (1987).

Dioxapyrrolomycin was reported to be primarily active against Gram-positive bacteria with some limited antifungal activity. The $LD_{50}$ was reported to be 13 mg/kg (po) and 125–250 mg/kg (ip) in mice, G. T. Carter, et al., J. Antibio. 40:233 (1987). The insecticidal activity of dioxapyrrolomycin is also known. ACS Meeting Abstracts 97, 98, 99 (Spring 1991).

G. T. Carter et al., J. Chem. Soc., Chem. Commun., 1989, pages 1271–1273, describes the biosynthesis of dioxapyrrolomycin.

N. Ezaki et al., J. Antibio., 34:1363–1365 (1981); M. Kaneda et al., J. Antibio., 34: 1366–1368 (1981); and M. Koyama et al., J. Antibio., 34:1569–1576 (1981); disclose the structures and synthesis of pyrrolomycins A and B.

M. Ishizuka, T. Sawa and T. Takeuchi, J. Antibio., 37:1253–1256 (1984), discloses the immunopotentiator activity of pyrrolomycin B.

K. Umezawa et al., Biochem. and Biophysic. Research Communic., 105:82–88, discloses enhancement of haemolysis and cellular arachidonic acid release by pyrrolomycins, such as pyrrolomycins A, B, C and D.

N. Ezaki et al., J. Antibio., 36:1263–1267 (1983), discloses pyrrolomycins C, D and E; and M. Koyama et al., J. Antibio., 36:1483–1489 (1983), discloses their structures.

U.S. Pat. No. 4,495,358 discloses antibiotic pyrrolomycin E prepared by culturing a Streptomyces sp. Pyrrolomycin A, B, C and D are also produced.

Derwent Abstract, Accession Number 83-755496, discloses antibiotics pyrrolomycin F, prepared by culturing Streptomyces sp.

N. Ezaki et at., J. Antibio., 36:1431–1438 (1983), discloses pyrrolomycins F1, $F_{2a}$, $F_{2b}$ and $F_3$, which are pyrrolomycin metabolites produced by the addition of bromide to the fermentation.

European Published Application 0 080 051 discloses 1-triiodoalkyl-allyl-pyrroles and analogues thereof having antifungal and antimicrobial activity, which are especially useful as antibacterial agents. These compounds were made as a result of structural modifications of pyrrolomycin A.

DETAILED DESCRIPTION OF THE INVENTION

The present invention particularly provides:

A method of killing or preventing the occurrence of parasitic worms in an animal hosting or susceptible to said worms comprising the administration to said animal of a therapeutic or prophylactic dosage of dioxapyrrolomycin.

Dioxapyrrolomycin is particularly effective against the following parasitic worms: Dictyocaulus, Haemonchus, Trichostrongylus, Ostertagia, Nematodirus, Cooperia, Bunostomum, Oesophagostomum, Chabertia, Strongyloides, Trichuris, Fasciola, Dicrocoelium, Enterobius, Ascaris, Toxascaris, Toxocara, Ascaridia, Capillaria, Heterakis, Ancylostoma, Uncinaria, Onchocerca, Taenia, Moniezia, Dipylidium, Metastrongylus, Hyostrongylus, and Strongylus. These worms most often occur in animals, such as sheep, swine, cattle, goats, dogs, cats, horses, poultry and man.

The present invention also provides:

An anthelmintic composition for administration to animals which comprises an effective anthelmintic amount of dioxapyrrolomycin.

Such a composition is useful in animals, such as sheep, swine, cattle, goats, dogs, cats, horses, poultry and man.

Lastly, the present invention provides:

In the process for producing dioxapyrrolomycin from a Streptomyces sp., the improvement which comprises:

the use of a culture medium comprising from about 10 to about 30 mg of starch, from about 10 to about 30 g of Solulys, from about 2 to about 8 g of meat extract, and from about 4 to about 6 g of sodium chloride, to culture the Streptomyces sp.

The preferred ingredients for the medium are the following: Difco soluble starch 20 g/l; Solulys 20 g; Beef extract 4 g; NaCl 5 g; tap water, quantity sufficient (qs) 1 liter; pH adjusted to 7.2 (KOH). This process may be further improved by the addition of the resin XAD-2 to the medium.

Pharmaceutically acceptable refers to those properties and/or substances which are acceptable to the patient from a pharmacological-toxicological point of view and to the manufacturing pharmaceutical chemist from a physical-chemical point of view regarding composition, formulation, stability, patient acceptance and bioavailability.

The present invention includes the anthelmintic use and anthelmintic compositions of dioxapyrrolomycin. Its structure is shown as Formula I in the Formula Chart below. Dioxapyrrolomycin is a known compound and may be prepared by the methods described in G. T. Carter, et at., J. Antibio. 40:233 (1987); H. Nakamara, et at. J. Antibio. 40:899 (1987). However, the present invention provides an improvement in the process for the preparation of dioxapyrrolomycin.

In G. T. Carter, et al., J. Antibio. 40:233 (1987), the medium employed in the tank fermentation consisted of molasses 20 g/l; dextrin 10 g; soy peptone 10 g; CaCO$_3$ 1 g; pH adjusted to 7.2 (KOH). The medium of the present invention employs CBS-10 which preferably comprises Difco soluble starch 20 g/l; Solulys 20 g; Beef extract 4 g; NaCl 5 g; tap water, quantity sufficient (qs) 1 l; pH adjusted to 7.2 (KOH). These ingredients are commercially available. The amounts of ingredients are approximate and may be varied as appropriate by one of ordinary skill in the art. Corn steep liquor or spray dried lard water may be used in place of Solulys. The use of this medium more than doubled the yield of dioxapyrrolomycin. The use of this medium plus the resin XAD-2, which is commercially available, not only doubled the yield of dioxapyrrolomycin, but also produced twice as pure compound, as did the medium alone. Other such neutral resins may be used, but XAD-2 is preferred.

Thus, in producing dioxapyrrolomycin for the present invention, the use of a neutral resin (XAD-2) as a titer enhancer was successfully employed. It was found that the addition of 50 g/L of XAD-2 in tank fermentations, more than doubled the amount of crude fermentation products that are extractable than when literature procedures alone are used. This increased product yield increases the amount of recoverable dioxapyrrolomycin even though the production of dioxapyrrolomycin has not increased relative to the other fermentation products.

The biological assays used to examine this compound included in vitro effects on the free-living nematode *Caenorhabditis elegans*, ability to clear target nematodes (*Haemonchus contortus* and *Trichostrongylus colubriformis*) from experimentally infected jirds, and clearance of *Haemonchus contortus* from monospecifically infected lambs, as described in more detail below.

Dioxapyrrolomycin is active in the *C. elegans* in vitro assay at 0.825 ppm. Table I shows results obtained for dioxapyrrolomycin against *H. contortus* and a second target parasite, *T. colubriformis* in the jird model. Dioxapyrrolomycin exhibited strong activity (≧90.9% clearance at 0.33 mg/jird=8.25 mg/kg; 96.4% clearance at 0.037 mg/jird= 0.925 mg/kg) against this parasite. It also is worth noting that although dioxapyrrolomycin is not highly active against *T. colubriformis*, it has a hint of activity (41.5% clearance at 0.33 mg/jird=8.25 mg/kg) against this parasite.

Table II shows results obtained for dioxapyrrolomycin in sheep against *H. contortus* (monospecific, experimental infections). Dioxapyrrolomycin exhibited potent activity (92.2% clearance of the worms at 1.56 mg/kg).

Having shown potent activity against *H. contortus* in sheep, dioxapyrrolomycin was examined for cross-resistance to the three major classes of broad-spectrum anthelmintics (ivermectin, levamisole, and benzimidazoles) using jirds infected with resistant strains of *H. contortus*. The data presented in Table III shows that dioxapyrrolomycin is equally efficacious against the resistant and nonresistant strains studied and hence is not cross-resistant to the major broad-spectrum anthelmintics. Dioxapyrrolomycin does, however, exhibit cross-resistance to closantel, a narrow-spectrum anthelmintic used in controlling *H. contortus*. In vitro, the dioxapyrrolomycin dose required to affect a closantel-resistant strain of *H. contortus* is approximately seventeen times that required for the susceptible strain.

In summary, dioxapyrrolomycin has activity of potential utility against the important ruminant parasite, *H. contortus*. Dioxapyrrolomycin appears to have some, albeit very weak, activity against a second ruminant parasite, *T. colubriformis*. Lack of cross-resistance with the three (3) major classes of broad-spectrum anthelmintics, but cross-resistance with the narrow-spectrum drug closantel, has been demonstrated for dioxapyrrolomycin.

Therefore, dioxapyrrolomycin is effective against worms, particularly parasitic worms of warm-blooded animals and more particularly helminth parasites in ovines (sheep) and bovines (cattle).

Dioxapyrrolomycin of Formula I can be used as the pure compound or as a mixture of pure compound, but for practical reasons, the compound is preferably formulated as an anthelmintic composition and administered as a single or multiple dose, alone or in combination with other anthelmintics (e.g. avermectins, benzimidazoles, levamisole, praziquantel, etc.). For example, aqueous or oil suspensions can be administered orally, or the compound can be formulated with a solid carrier for feeding. Furthermore, an oil suspension can be converted into an aqueous emulsion by mixing with water and injecting the emulsion intramuscularly, subcutaneously or into the peritoneal cavity. In addition, dioxapyrrolomycin (which hereafter may be referred to as the "active compound") can be administered topically to the animal in a conventional pour-on formula.

Pure active compound, mixtures of the active compound, or combinations thereof with a solid carrier can be administered in the animal's food, or administered in the form of tablets, pills, boluses, wafers, pastes, and other conventional unit dosage forms, as well as sustained/controlled release dosage forms which deliver the active compound over an extended period of days, weeks or months. All of these various forms of the active compound of this invention can be prepared using physiologically acceptable carriers and known methods of formulation and manufacture.

Representative solid carriers conveniently available and satisfactory for physiologically acceptable, unit dosage formulations include corn starch, powdered lactose, powdered sucrose, talc, stearic acid, magnesium stearate, finely divided bentonite, and the like. The active compound can be mixed with a carrier in varying proportions from, for example, about 0.001 percent by weight in animal feed to about 90 or 95 percent or more in a pill or capsule. In the latter form, one might use no more carrier than sufficient to bind the particles of active compound.

In general, the active compound can be formulated in stable powders or granules for mixing in an amount of feed for a single feeding or enough feed for one day and thus obtain therapeutic efficacy without complication. It is the prepared and stored feeds or feed premixes that require care. A recommended practice is to coat a granular formulation to protect and preserve the active compound. A prepared hog-feed containing about 0.02 percent of the active compound will provide a dosage of about 10 mg per kg body weight for each 100 lb pig in its daily ration.

A solid diluent carrier need not be a homogeneous entity, but mixtures of different diluent carriers can include small proportions of adjuvants such as water; alcohols; protein solutions and suspensions like skimmed milk; edible oils; solutions, e.g., syrups; and organic adjuvants such as propylene glycols, sorbitol, glycerol, diethyl carbonate, and the like.

The solid carrier formulations of the active compound are conveniently prepared in unit dosage forms, to facilitate administration to animals. Accordingly, several large boluses (about 2 g weight) amounting to about 4.1 g of active compound would be required for a single dosage to a 900 lb horse at a dosage rate of 10 mg/kg of body weight. Similarly, a 60 lb lamb at a dosage rate of 10 mg/kg of body weight would require a pill, capsule, or bolus containing about 0.3 g of active compound. A small dog, on the other hand, weighing about 20 lbs. would require a total dosage of about 90 mg at a dosage rate of 10 mg/kg of body weight. The solid, unit dosage forms can be conveniently prepared in various sizes and concentrations of active compound, to accomodate treatment of the various sizes of animals that are parasitized by worms.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as cationic, anionic, or non-ionic surface-active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, sodium carboxymethylcellulose, methylcellulose, sodium polyvinylpyrrolidone, and the like. The proportion of the active compound in the aqueous suspensions of the invention can vary from about 1 percent to about 20 percent or more.

Oil solutions are prepared by mixing the active compound and an oil, e.g. an edible oil such as cottonseed oil, peanut oil, coconut oil, modified soybean oil, and sesame oil. Usually, solubility in oil will be limited and oil suspensions can be prepared by mixing additional finely divided active compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound. At present, it is known that doses of 1.56 to 12.5 mg/kg of body weight in sheep of dioxapyrrolomycin will effectively combat *H. contortus*. Effective therapeutic and prophylactic dosages are contemplated in the range of about 2 to about 20 mg/kg of body weight.

In other animals, and for other kinds of parasitic worms, definitive dosages can be proposed. Contemplated are dosage rates of about 1 mg to about 20 mg/kg of body weight. A preferred, contemplated range of dosage rates is from about 5 mg to about 10 mg/kg of body weight. In this regard, it should be noted that the concentration of active compound in the formulation selected for administration is in many situations not critical. One can administer a larger quantity of a formulation having a relatively low concentration and achieve the same therapeutic or prophylactic dosage as a relatively small quantity of a relatively more concentrated formulation. More frequent small dosages will likewise give results comparable to one large dose. One can also administer a sustained release dosage system (protracted delivery formulation) so as to provide therapeutic and/or prophylactic dosage amounts over an extended period. Unit dosage forms in accordance with this invention can have anywhere from less than 1 mg to 50 g of active compound per unit.

Although dioxapyrrolomycin will find its primary use in the treatment and/or prevention of helminth parasitisms in domesticated animals such as sheep, cattle, horses, dogs, swine, goats and poultry, it is also effective in treatment that occurs in other warm blooded animals, including humans. The optimum amount to be employed for best results will, of course, depend upon species of animal to be treated, the regimen treatment and the type and severity of helminth infection. Generally good results are obtained with dioxapyrrolomycin by the oral or parenteral route of administration of about 1 to 10 mg/kg of animal body weight (such total dose being given at one time, in a protracted manner or in divided doses over a short period of time such as 1–4 days). The technique for administering these materials to animals are known to those skilled in the veterinary and medical fields.

It is contemplated that dioxapyrrolomycin can be used to treat various helminth diseases in humans, including those caused by Ascaris, Enterobius, Ancylostoma, Trichuris, Strongyloides, Fasciola, Taenia, and/or Onchocerca or other filariae at a dose of from 1 to 20 mg/kg of body weight upon oral and/or parenteral administration.

The following detailed examples/procedures describe the biological testing and production of dioxapyrrolomycin and are to be construed as merely illustrative, and not limitations of the preceding disclosure in any way whatsoever. Those skilled in the art will promptly recognize appropriate variations from the procedures.

DESCRIPTION OF THE PREFERRED EMBODIMENTS

EXAMPLE 1 *Caenorhabditis elegans* Assay

The free-living nematode *C. elegans* in vitro assay has been described extensively in the literature, for example, K. G. Simpkin and G. C. Coles, J. Chem. Tech. Biotechnol., 31:66–69 (1981).

Dioxapyrrolomycin is active in the *C. elegans* assay at 0.825 ppm.

EXAMPLE 2 *Haemonchus contortus/Trichostrongylus colubriformis*/Jird Assay:

This in vivo assay utilizes jirds infected with two important target parasites of ruminants, *H. contortus* and *T. colubriformis* (anthelmintic-sensitive or -resistant worms can be used). Initially, activity is assessed only against *H. contortus* as described in G. A. Conder et. al., J. Parasitol. 76:168–170 (1990), while follow-up studies examine activity against both species of parasites using the techniques outlined in G. A. Conder et at., J. Parsitol. 77:168–170 (1991).

Table I shows results obtained for dioxapyrrolomycin in the jird model.

EXAMPLE 3 Haemonchus contortus/Sheep Assay:

Purpose bred, helminth-free lambs are procured. Upon ardvai, the lambs are treated with ivermectin (0.2 mg/kg, subcutaneously), vaccinated for sore mouth, and placed in a single, community pen. Three weeks later each lamb is treated with levamisole hydrochloride (8.0 mg/kg per os). Two weeks after treatment with levamisole, all lambs are inoculated per os with—7,500 infective larvae of *H. contortus*. Rectal fecal samples are taken from each lamb 1 to 3 days prior to infection and these are examined using the double centrifugation technique to verify that the animals are free of trichostrongyles prior to infection. On day 32–34 postinoculation (PI), a rectal fecal sample from each lamb is examined again using the McMaster counting chamber technique to verify infection; those animals which do not exhibit suitable infection are dropped from the study. Remaining lambs are treated per os on day 35 PI; 4–5 animals receive vehicle only. Prior to administration, test materials are prepared in a manner suitable for the substance being examined. All lambs are monitored for toxic signs following treatment. Lambs are killed 7 days after treatment (day 42 PI), and the abomasum is ligated and removed from each animal. Each abomasum is opened longitudinally and the contents rinsed into an 80 mesh sieve. Sieve contents are collected in individual containers and fixed in formol-alcohol. Later each sample is transferred to a 1,000 ml graduated cylinder and the volume brought to 400–1000 ml with tap water. The total number of worms in a 10% aliquot is determined. If no worms are found in the 10% aliquot, the entire sample is examined. Total worm number/lamb and percentage clearance for each treatment are calculated. Percentage clearance is determined according to the following formula: Percentage clearance=[(Mean number of worms recovered from vehicle control lambs—number of worms recovered from treated lamb)/mean number of worms recovered from vehicle control lambs]×100. A substance is considered highly active if its clearance is ≧90% and moderately active if its clearance is ≧70 but <90%.

Table II shows results obtained for dioxapyrrolomycin in sheep against *H. contortus* (monospecific, experimental infections).

EXAMPLE 4 Production and Isolation of Dioxapyrrolomycin

Bacterial Culture

Streptomyces sp. 90413 (strain number in Upjohn Culture Collection, 90413, UC® 11065, The Upjohn Co., Kalamazoo, Mich.) is isolated from Michigan soil and maintained as frozen agar plugs of vegetative growth in a liquid nitrogen vapor phase. It is believed that other known dioxapyrrolomycin-producing Streptomyces sp., such as those identified in G. T. Carter, et al., J. Antibio. 40:233 (1987), and H. Nakamura, et at., J. Antiobio. 40:899 (1987), would be suitable substitutes for the above species in the process of the present example.

Fermentation Conditions

Primary fermentations in medium CBS 10 are carded out in 100 ml volumes in shaken flasks. Shake flask fermentations are run for 72 hours in 100 ml volumes in 500 ml wide-mouth flasks at 28° C. (250 rpm, 1.5 inch throw). Shake flask pools (2 and 3 liter) are inoculated from 100 mi seed shake flask cultures (medium GS-7:25 g/l cerelose, 25 g/l Pharmamedia, pH=7.2 with $NH_4OH$, autoclaved 30 minutes) at a 5% (v/v) rate.

Production Fermentations using Neutral Resins

The organism is inoculated into medium GS-7. The inoculated 100 ml volumes of GS-7 are fermented for 72 hours as described above. The mature seed cultures are used as the source of inoculum (5% seed rate) for the fermentation medium (CBS 10 containing XAD-2). CBS-10 is composed of Difco soluble starch 20 g; solulys, 20 g; beef extract 4 g; NaCl 5 g; and tap water, quantity sufficient (qs) 1l. Neutral resin (XAD-2) is incorporated into CBS 10 before autoclaving in flasks at a final concentration of 60 g/l. In tank fermentations, sterile XAD-2 is added 2–3 hours post inoculation at a final concentration of 50 g/l. The pH of the fermentation medium is adjusted to 7.2 using KOH before autoclaving (30 min/flask, 90 min/tank). Inoculated flask fermentations are employed in the manner described for GS-7 above for four days of fermentation. Inoculated 10 L tank fermentations (Labraferm) are stirred at 250 rpm at 28° C. with an air flow rate of 6–7 l/min for 4–5 days of fermentation.

Sample Preparation, Assay and Harvesting

Assay samples from shake flask fermentations (1.5 ml) are centrifuged and the clear supernatants are transferred to 1.2 ml microtubes. Samples are assayed for activity as described in the examples above.

Extraction Procedure

Filter whole beer at harvest pH (celaton FW-40 filter aid may be used if desired). The clear filtrate may be discarded. Process the mycelial cake as described below. The XAD-2 resin remains in the mycelial cake during filtration and should be processed as part of the cake.

Trituration of the Mycelial Cake with Acetone

1. Stir mycelial cake three times with ⅙ original beer volumes of acetone each time (ACETONE-1 ,-2,-3). Combine acetone extracts 1, 2 & 3 and process as described below.

Extraction of Aetone Pool

1. Add ½ pool volume of methylene chloride to the acetone pool. Separate organic phase (lower) from the aqueous acetone phase (upper). Aqueous phase may be discarded. Dry $MeCl_2$/acetone organic phase over $Na_2SO_4$ and concentrate to an oil in vacuo (preparation A). Preparation A should then be fractionated by silica gel column chromatography as described below.

Silica Gel Column Chromatography

1. An open silica gel (70-230 mesh) column* is poured and equilibrated in two bed volumes of n-hexane. Preparation A from above is absorbed onto 2 times its weight of silica gel and loaded onto the head of the column.

*25 grams silica gel per gram of crude preparation A

2. The silica gel column is then eluted** in the following manner:

start: 2 - bed volumes n-hexane 4 - bed volumes 85 hexane: 15 EtOAc end: 2 - bed volumes EtOAc

**CAUTION: As the 85 hexane: 15 EtOAc is introduced to the column, heat is generated within the column.

3. Silica column pools are collected in bed volume aliquots as described below:

Pool A: bed volumes 1 & 2 (discard)
Pool B: bed volume 3
Pool C: bed volume 4
Pool D: bed volume 5
Pool E: bed volume 6
Pool F: bed volumes 7 & 8

4. The above silica column pools B - F are then concentrated to dryness in vacuo. Pool D will contain the majority of dioxapyrrolomycin and will be referred to as preparation B. Pools C and E may contain small quantities of dioxapyrrolomycin. Verification of silica pool compositions may be done by the analytical HPLC procedure described below.

Analytical HPLC of Preparation B

1. Analytical HPLC for sample analysis and peak identification was performed on a Hewlett Packard (HP) 1090A with Diode Array Detector (DAD) and HP PC work station. Separation was performed on an HP 2.1 mm×200 mm ODS (Hypersil) RP (5 um) column preceded by an HP ODS guard column. Elution was achieved with isocratic 65% ACN:35% NH$_4$OAc (pH=4.0) for 5.0 minutes followed by a 20 minute linear gradient to 100% ACN. Column temperature was maintained at 65° C. and column eluant was monitored by UV detection @240 nm. Mobile phase flow rate was maintained at 0.5 ml/min throughout the entire separation. Sample injections of 1.0–25.0 mcl were performed automatically by the HP 1090A HPLC.

The relative retention time of dioxapyrrolomycin under these analytical HPLC parameters is 1.4 minutes and peak identification is verified by dioxapyrrolomycin's characteristic UV spectrum recorded by the DAD. Once the composition of preparation B has been verified by analytical HPLC, the final recovery of pure dioxapyrrolomycin from preparation B was carried out by preparative HPLC as described below.

Preparative HPLC Purification of Dioxapyrrolomycin from Preparation B

Preparative HPLC for purification of dioxapyrrolomycin from preparation B was performed on a Waters prep LC 3000 with a variable wavelength UV/VIS detector and Waters 745B integrator. Separation was performed on three Waters Radial Pak C-18 (25×100 mm) columns in series with a Waters 25×10 mm Radial Pak C-18 guard column. Elution was achieved with isocratic 60% ACN: 40% NH$_4$OAc (pH=4.0) for 25 minutes. Column was maintained at ambient temperature with column eluant monitored by UV detection @254 nm. Mobile phase flow rate was maintained at 34.2 ml/min throughout the entire separation. Sample injections were pumped directly onto the head of the column with maxima injection volumes of 50.0 ml.

The retention time of dioxapyrrolomycin under these preparative HPLC parameters ranges between 9.00 and 12.00 minutes depending on sample load. Baseline resolution of dioxapyrrolomycin is achievable under these parameters; however, purity of preparative HPLC fractions should be checked by analytical HPLC analysis prior to pooling of preparative fractions. Excess NH$_4$OAc buffer from the preparative HPLC procedure was removed from the sample by absorbing the dioxapyrrolomycin onto HP-20 resin and washing of the resin with water. The dioxapyrrolomycin was then recovered from the resin by extraction with MeOH. Crystalline dioxapyrrolomycin (preparation C) is the resulting product of this final purification stage.

Verification of the structure of preparation C, was then accomplished by the spectroscopic and analytical analysis described below.

Identification of Dioxapyrrolomycin

Preparation C (1) was obtained as fine yellow needles. The UV spectrum of 1 suggested 1 is structurally related to pyrrolomycins. Computer search of the IR spectrum of 1 against the spectrum library identified dioxapyrrolomycin as the most likely structure. Comparison of these spectra, with published UV and IR spectrum of dioxapyrrolomycin showed that they are virtually superimposable.

The elemental analysis results (37.4% C, 1.5% H, 7.0% N, 36.5% Cl) of 1 are consistent the molecular formula of dioxapyrrolomycin ($C_{12}H_6N_2O_4Cl_4$) which predicts 37.5% C, 1.6% H, 7.35 N, 37.0% Cl).

FAB-MS spectrum of 1 displayed a weak ion cluster (m/e=382, 384, 386), expected for the (M+H)$^+$ions of dioxapyrrolomycin. The most intense peaks at 306, 308, and 310 represent the loss of one nitro and one formaldehyde (M—NO$_2$—CH$_2$O) from molecular ions.

The HMR spectrum (obtained in CDCl3) of 1 displayed only one exchangeable proton at 9.14 ppm, due to the pyrrole proton. The higher field position of this proton, compared to the similar situated proton in pyrrolomycin C, is attributed to the absence of a neighboring carbonyl group. A total of five non-exchangeable protons were detected between 5 and 8 ppm region. The AB quartet (5.58, 5.37 ppm, J=6.2 Hz) is consistent with the presence of a mythylenedioxy group. The sharp singlet (6.85 ppm) is consistent with the presence of a carbinol proton sandwiched between two aromatic systems. The two long-ranged coupled protons at 7.31 and 6.88 ppm (J=2.1 Hz) are consistent with the presence of a 1,2,3,5 tetrasubstituted phenyl group. Again, the relative deshielding of these two protons, compared to pyrrolomycin C, is attributed to the reduction of the carbonyl group to the methyleneoxy functionality.

The CMR signals of 1 (75 MHz, deuterated MeOH) are as follows: δ 146.2 (s), 131.5(s), 130.5(d), 130.4(s), 127.3 (s), 126.1(d), 125.5(s), 124.0(s), 117.5(s), 106.0(s), 92.3(t) and 70.4(d). While all of above signals (chemical shift and multiplicities) agree well with the structure of dioxapyrrolomycin, small differences were observed between these and the reported values (8) (obtained in CDCl3) as a result of solvent effects.

Since the structure of dioxapyrrolomycin contains an optical center, ORD of 1 was obtained (c=2.23, MeOH) to determine the chirality of 1. The result (−77°) is in fair agreement with the reported value (−88°) of dioxapyrrolomycin therefore indicated that 1 has same absolute configurations as that of dioxapyrrolomycin.

TABLE I

Percentage Clearance of *Haemonchus contortus* and *Trichostrongylus colubriformis* from jirds inoculated per os with −1,000 exsheathed, infective larvae of each parasite, treated per os with dioxapyrrolomycin on day 10 postinoculation (PI) and necropsied on day 13 postinoculation.

| Compound (Reference) | Purity | Dose (mg/jird) | n (survived to necropsy) | Percentage Clearance | |
|---|---|---|---|---|---|
| | | | | *H. contortus* | *T. colubriformis* |
| Dioxapyrrolomycin | ~100% | 0.33 | 3(1) | 90.9 | 41.5 |
| | | 0.33 | 3(3) | 100 | 41.5 |
| | | 0.11 | 3(3) | 100 | 0 |
| | | 0.037 | 3(3) | 96.4 | 17.2 |
| | | 0.012 | 3(3) | 45.8 | 48.8 |

TABLE II

Percentage clearance of *Haemonchus contortus* from lambs monospecifically inoculated per os with ~7,500 infective larvae of the parasite, treated per os with dioxapyrrolomycin on day 35 post-inoculation (PI), and necropsied on day 42 PI.

| Compound (Reference) | Purity | Dose (mg/kg) | Percentage Clearance |
|---|---|---|---|
| Dioxapyrrolomycin | ~100% | 12.5 | 100 |
|  |  | 6.25 | 99.9 |
|  |  | 3.125 | 99.7 |
|  | ~100% | 3.125 | 99.9 |
|  |  | 1.56 | 92.2 |
|  |  | 0.78 | 44.0 |

TABLE III

Percentage clearance of susceptible, levamisole/benzimidazole-resistant, or ivermectin-resistant *Haemonchus contortus* from jirds inoculated per os with ~1,000 exsheathed, infective larvae of a particular strain of the parasite, treated per os with dioxapyrrolomycin, levamisole hydrochloride, albendazole, or ivermectin on day 10 postinoculation (PI), and necropsied on day 13 PI.

| Compound (Reference) | Purity | Dose (mg/jird) | Percentage Clearance | | |
|---|---|---|---|---|---|
|  |  |  | Susceptible | Levamisole/ Benzimidazole Resistant | Ivermectin Resistant |
| Dioxapyrrolomycin | 95%* | 0.11 | 95.8 | 98.6 | 92.7 |
| Levamisole hydrochloride |  | 0.4 | ~95.0 | 51.7 | 96.4 |
| Albendazole |  | 0.075 | ~95.0 | 36.2 | N.D. |
| Ivermectin |  | 0.005 | ~95.0 | 98.6 | 18.7 |

*Pyrrolomycin C makes up the majority of the remainder.
N.D. = Not Done.

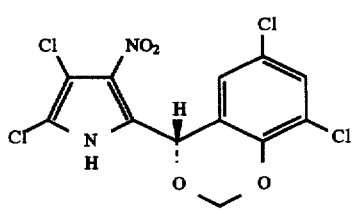

We claim:

1. A method of killing parasitic worms in an animal hosting said worms comprising the administration to said animal of a therapeutic dosage of dioxapyrrolomycin, wherein the parasitic worms are Dictyocaulus, Haemonchus, Trichostrongylus, Ostertagia, Nematodirus, Cooperia, Bunostomum, Oesophagostomum, Chabertia, Strongyloides, Trichuris, Fasciola, Dicrocoelium, Enterobius, Ascaris, Toxascaris, Toxocara, Ascaridia, Capillaria, Heterakis, Ancylostoma, Uncinaria, Onchocerca, Taenia, Moniezia, Dipylidium, Metastrongylus, Hyostrongylus, or Strongylus.

2. The method of claim 1 wherein the animals are sheep, swine, cattle, goats, dogs, cats, horses, poultry or man.

3. The method of claim 2 wherein the therapeutic dosage is 2–20 mg/kg.

* * * * *